United States Patent
Bailey et al.

(10) Patent No.: US 9,421,303 B2
(45) Date of Patent: Aug. 23, 2016

(54) FUSION OF BIOCOMPATIBLE GLASS/CERAMIC TO METAL SUBSTRATE

(71) Applicant: Covalent Coating Technologies, LLC, East Hartford, CT (US)

(72) Inventors: Orville G. Bailey, East Hampton, CT (US); Gary Fischman, Gambrills, MD (US); Petre Bajenaru, Westborough, MA (US)

(73) Assignee: Covalent Coating Technologies, LLC, East Hartford, CT (US)

( * ) Notice: Subject to any disclaimer, the term of this patent is extended or adjusted under 35 U.S.C. 154(b) by 0 days.

(21) Appl. No.: 14/199,293

(22) Filed: Mar. 6, 2014

(65) Prior Publication Data

US 2014/0255593 A1    Sep. 11, 2014

Related U.S. Application Data

(60) Provisional application No. 61/773,426, filed on Mar. 6, 2013.

(51) Int. Cl.
 *C23D 5/02* (2006.01)
 *A61L 27/06* (2006.01)
 (Continued)

(52) U.S. Cl.
 CPC ............... *A61L 27/306* (2013.01); *A61L 27/06* (2013.01); *A61L 27/54* (2013.01); *C23C 24/10* (2013.01);
 (Continued)

(58) Field of Classification Search
 CPC ............ A61F 2310/00928; A61L 27/30; C03C 4/0007; C03C 3/04
 USPC ............... 427/2.27, 377, 376.4, 376.2
 See application file for complete search history.

(56) References Cited

U.S. PATENT DOCUMENTS 2,843,500 A * 7/1958 Harman et al. ............... 428/433
3,441,422 A * 4/1969 Graff ............................. 501/76
(Continued)

FOREIGN PATENT DOCUMENTS

DE    2600631    7/1977
DE    44198381   12/1995
(Continued)

OTHER PUBLICATIONS

Pajamaki et al. Bioactive glass and glass-ceramic-coated hip endoprosthesis: experimental study in rabbit. Journal of Materials Science Materials in Medicine 6(1995) 14-18.*
(Continued)

*Primary Examiner* — Cachet Sellman
(74) *Attorney, Agent, or Firm* — Donald S. Holland, Esq.; Holland & Bonzagni, P.C.

(57) ABSTRACT

Applicants have disclosed a process for fusing a biocompatible glass to a metal substrate. In the preferred embodiment, the process comprises: grit blasting a metallic substrate (e.g., titanium) to remove a surface layer of the metal; after blasting, cleaning the abrasion residue off the surface layer; blending a solvent to use as a suspension agent; creating a suspension of biocompatible and bioactive glass-coating powders in the solvent solution; depositing the suspension onto the metallic substrate; drying thoroughly the suspension-coated metallic substrate; inserting the dried, coated substrate into a non-reactive chamber, purging the chamber with an inert gas, such as pure argon; and firing the metallic substrate, inside the furnace, in the inert gas. This process forms a robust fusion between the biocompatible glass and titanium, according to preliminary test results. This process can be used for various medical and dental devices, including implants and onplants.

9 Claims, 3 Drawing Sheets

(51) Int. Cl.
*A61L 27/30* (2006.01)
*A61L 27/54* (2006.01)
*C23D 7/00* (2006.01)
*C23C 24/10* (2006.01)
*C23D 9/00* (2006.01)

(52) U.S. Cl.
CPC .. *C23D 5/02* (2013.01); *C23D 7/00* (2013.01); A61L 2300/10 (2013.01); A61L 2420/02 (2013.01); A61L 2430/02 (2013.01); *C23D 9/00* (2013.01)

(56) References Cited

U.S. PATENT DOCUMENTS

| | | | | |
|---|---|---|---|---|
| 3,803,875 | A | * | 4/1974 | Root et al. .......................... 65/43 |
| 4,159,358 | A | * | 6/1979 | Hench et al. ................... 427/318 |
| 4,476,156 | A | * | 10/1984 | Brinker et al. ............. 427/126.2 |
| 4,613,516 | A | * | 9/1986 | Kucheria .............. A61L 27/306 427/2.27 |
| 6,087,018 | A | * | 7/2000 | Uchiyama ..................... 428/469 |
| 8,012,590 | B2 | | 9/2011 | Tomsia et al. |
| 8,119,183 | B2 | * | 2/2012 | O'Donoghue ...... A61F 2/30767 427/180 |
| 2008/0118745 | A1 | * | 5/2008 | Endres et al. ................. 428/336 |
| 2012/0234391 | A1 | * | 9/2012 | Boussaad et al. ............. 136/262 |

FOREIGN PATENT DOCUMENTS

| | | |
|---|---|---|
| EP | 153863 | 9/1985 |
| EP | 264917 | 4/1988 |
| EP | 368101 | 5/1990 |
| GB | 2135987 | 9/1984 |
| JP | 2002120495 | 4/2002 |
| WO | 2005066388 | 7/2005 |
| WO | 2012037242 | 3/2012 |

OTHER PUBLICATIONS

Braem et al. Bioactive glass—ceramic coated titanium implants prepared by electrophoretic deposition. Materials Science and Engineering C (Impact Factor: 3.09). Jun. 2012; 32(8).*

* cited by examiner

FUSION OF BIOCOMPATIBLE GLASS/CERAMIC TO METAL SUBSTRATE

RELATED APPLICATION

This application claims priority to U.S. Provisional Patent Application Ser. No. 61/773,426, filed Mar. 6, 2013. Applicants claim priority from that application. Applicants also incorporate by reference that application in its entirety.

FIELD OF INVENTION

This invention deals in general with adhering a type of amorphous ceramic to a different substrate. More particularly, it relates to bonding biocompatible and bioactive glass to medical products and devices (e.g., implants, onplants and diagnostic) which later come in contact with physiological fluids.

BACKGROUND OF THE INVENTION

Currently there is limited success in achieving full adhesion of biocompatible glasses to the parent metal (e.g., common titanium alloys). Current processes do not yield a consistent ionocovalent bond in the molecular structure, as disclosed in U.S. Pat. No. 8,012,590 to Tomsia et al. Various researchers and technologist have attempted to coat metallic implants with biocompatible glasses using enameling, rapid immersion in molten glass, or plasma spraying techniques. Although some coatings with excellent in-vitro behavior were obtained, the coatings were characterized by cracking and poor integrity of the glass-to-metal interface. These imperfect coatings were due to undesirable covalent oxides inherent in the processing techniques.

Tenacious coatings made with glass on a titanium alloy, or on some other metals, are known to have limited success. There are a variety of defects that could lead to faulty surfaces. For coated metal implants and onplants, a defective coating poses a health risk. A successful coating technology requires that the body not reject or become infected due to the device. Homogeneity of the metal and any coating applied, and continuity of that coding within the design, is required to assure there is no gap for foreign substance; bacteria, viruses, food or the like to lodge and create infection.

Coatings are applied to present a function for the body; be it tissue growth, simulation of tissue (e.g., bone, tooth), or presentation of medications. The coating must be appropriately integrated with the substrate material so that it does not fail by loosening from the substrate (i.e., delamination). Many coated devices are in the field and each has a risk of coating delamination.

One approach to adhering the coating to the metal substrate is by chemically bonding the material to the substrate versus mechanically bonding to the substrate. This is done by preparing both the substrate and biocompatible glass to create an interface that is stronger than previous interfaces attempted by other glass to metal systems.

Accordingly it is a primary object of the present invention to bond biocompatible ceramic (e.g., glass) to a medical device or product in such a way as to minimize delamination.

It is another object to apply biocompatible glass/ceramic to a metallic substrate to produce a homogeneous glass surface upon the substrate without gaps or other defects between the coating and substrate.

It is a more specific object, commensurate with the above-listed objects, to fuse a biocompatible and bioactive ceramic (e.g., glass) to a metal substrate to produce a tenacious coating for a medical product, which is safe and durable to use.

SUMMARY OF THE INVENTION

Applicants have invented a method for applying biocompatible and bioactive glasses to dissimilar materials—namely, titanium or other specialty metal substrates—which ensures an impervious seal of the ceramic or glass to metal to avoid breakdown of the coating (e.g., by delamination).

In the preferred embodiment, Applicants' process comprises: grit blasting a metallic substrate to remove a surface layer of the metal; after blasting, cleaning any abrasion residue off the metal; blending a solvent to use as a suspension agent; creating a suspension of glass-coating powders in the solvent solution; depositing the suspension onto the metallic substrate by, e.g.: spraying; drying thoroughly the suspension-coated metallic substrate; inserting the dried substrate into a non-reactive chamber, purging the chamber with an inert gas, such as pure argon; and firing the metallic substrates, inside the furnace.

BRIEF DESCRIPTION OF THE DRAWINGS

The above objects and other advantages of the invention will become more readily apparent upon reading the following description and drawings, in which.

DETAILED DESCRIPTION OF THE PREFERRED EMBODIMENT

Referring to FIGS. 1-5 in detail, Applicants have disclosed a preferred method for fusing a glass coating deposited on a metal (e.g., titanium) surface of a medical or dental component to be implanted or onplanted. The resultant coating forms a strong, chemical bond to the metal surface that requires an unreasonable quantity of effort and equipment to remove (see FIG. 5). Such a coating provides protection for the metal substrate, component-biologic system compatibility, and serves as a bone conversion source provided the proper chemical constitution is included in the glass.

As used herein, the terms "implanted medical device" and "implantable medical device" refer to medical devices that are designed to be at least partially placed within a patient's body. Typically, such devices, or portions thereof, are placed within the patient's body for a period of time for which it could be beneficial to have a therapeutic agent present on the external surface of the device. For example, a medical device implanted in a patient's body for several hours, or more, constitutes an implantable medical device for the purposes of this disclosure.

As used herein, the terms "onplant", "onplanted" and "onplanted medical device" refer to medical devices fixed to the surface of a biological structure often to augment that structure. For example, an onplant can be an orthodontic anchorage device fixed to a bone surface or a contact lens.

Figure 1:
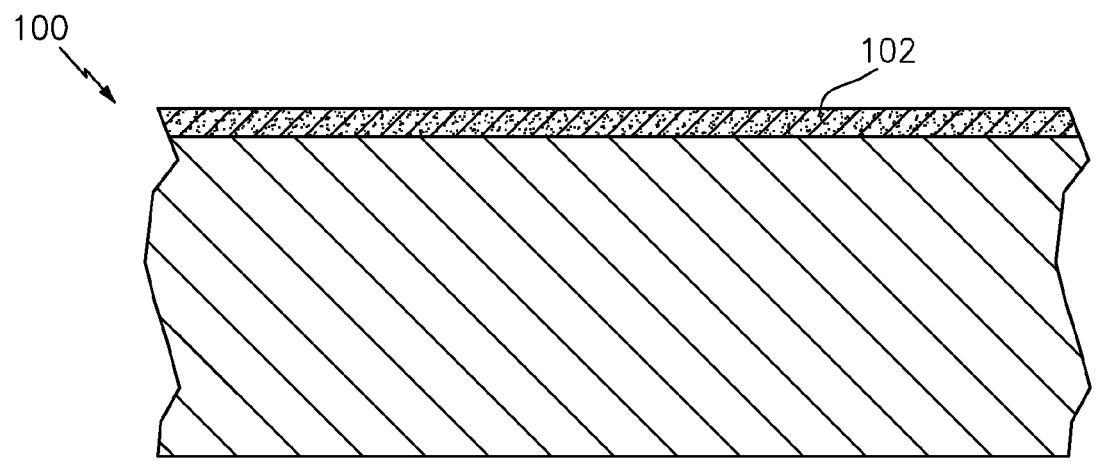
FIG. 1 depicts a cross-sectional view of a passivated substrate of metal (titanium) with an oxide layer.
Figure 2:
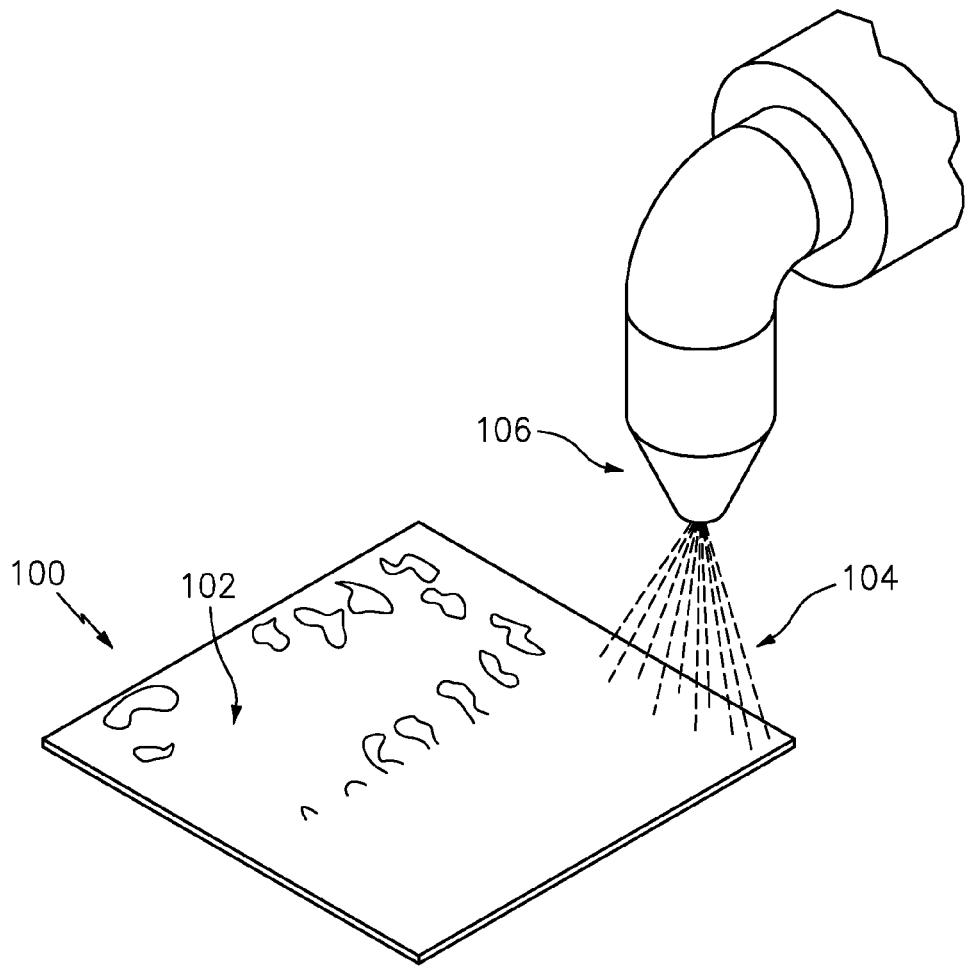
FIG. 2 depicts a micro-structural cleaning (here, grit blasting) of the titanium substrate.
Figure 3:
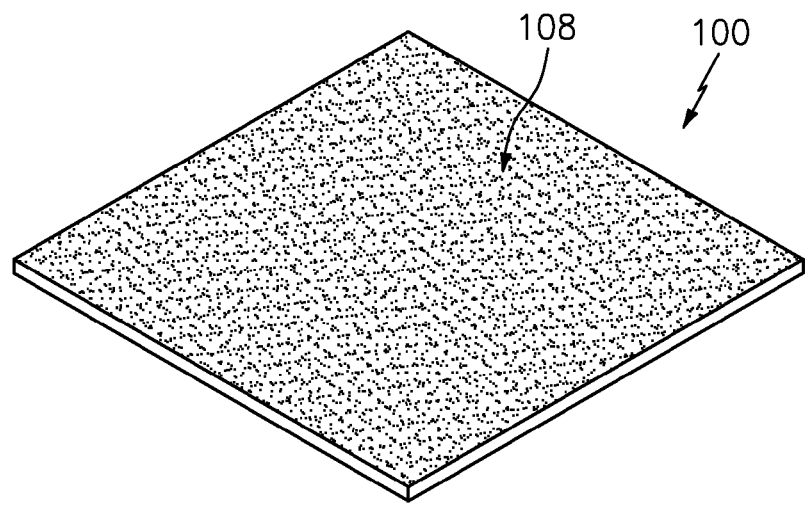
FIG. 3 depicts an ablated titanium substrate after micro-structural cleaning.

Referring to FIGS. 1 and 2, the illustrated sample titanium 100 has a surface layer 102 which is passivated. Titanium oxide has bonded, due to atmosphere, onto the titanium 100. The passivation is inherent in the fabrication of the metal. Most metals chemically bond with oxygen, nitrogen, or other reactive elements found in the environment when it is created at the metal foundry. If removed, the passivation layer will re-form on the unprotected ablated substrate due simply to the chemical affinity to form.

Figure 4:
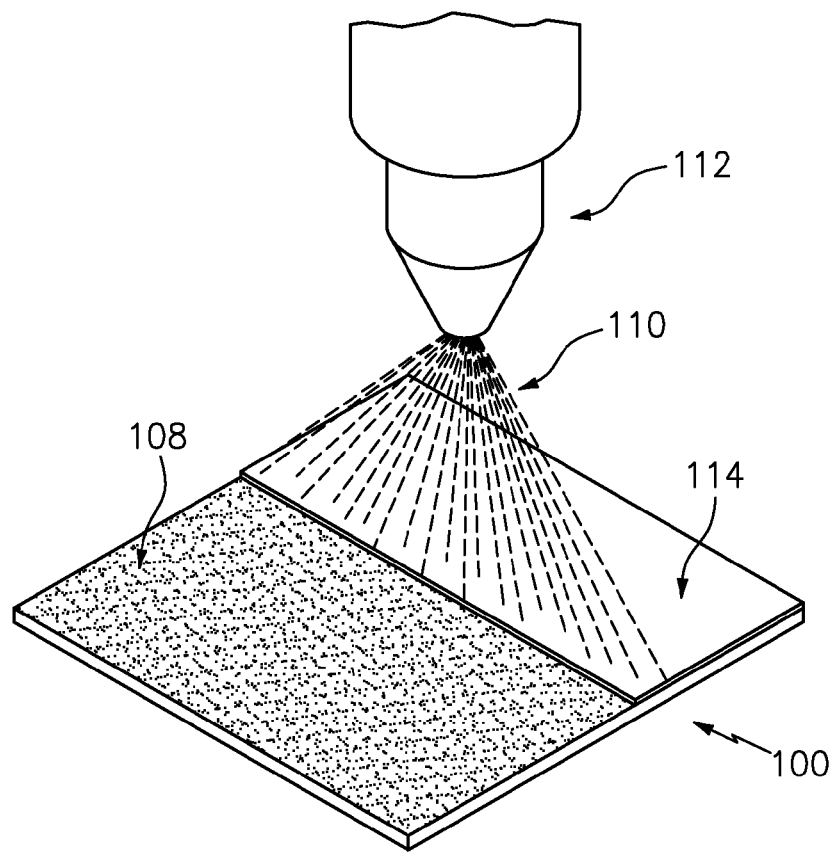
FIG. 4 depicts spraying a coating of biocompatible and bioactive glass onto a cleaned, ablated substrate.

Applicants' preferred process comprises the following steps:
a. Grit blasting a metallic substrate (e.g., the illustrated titanium 100) with preferably aluminum oxide (i.e., 220 or greater grit size) 104, or with a similar ceramic oxide media, via nozzle 106 to remove a surface layer (e.g., 102 in FIG. 1) of the metal 100 so as to minimize the introduction of active foreign particles. See FIG. 2. This step leaves an ablated metal surface 108 shown in FIG. 3;
b. Post-grit blasting, cleaning the abrasion residue via an ultrasonic bath, preferably using alcohol (not shown);
c. Blending a solvent solution of 90%-99% propanol in organic alcohol;
d. Creating a suspension of glass-coating powders in the solvent solution. The concentration of the suspension varies depending on desired coating thickness;
e. Spraying the suspension 110 onto the cleaned, ablated, metallic surface 108 with an air brush 112 at 10-20 psi, until the surface 108 is fully coated. See FIG. 4. Part of the coating is shown in FIG. 4 at 114;
f. Drying the suspension-coated metallic substrate thoroughly in air;
g. Inserting the dried, coated substrate into a non-reactive chamber of an atmospheric furnace (not shown), and substantially purging the chamber with pure inert gas, preferably argon. Minimal traces of air, oxygen or nitrogen might be present after purge;
h. Firing the coated metallic substrate, inside the furnace, in the inert gas (not shown). The firing parameters should be fully dependent on the desired glass thermal characteristics; and
i. Slow cooling the fired coated metallic substrate to minimize stress between the glass and metal substrate. See FIG. 5 for final product 116.

As used with Applicants' preferred method, a bioactive glass may contain, but is not limited to, the following components: CaO, $SiO_2$, $Na_2O$ and, $P_2O_5$. (Similar chemistries can be used for borosilicate glasses.) If the glass to be used is biocompatible (and not bioactive), it may contain, but is not limited to, the following components based on the requirement of the application: F, $ZrO_2$, ZnO, CaO, $K_2O$, $SiO_2$, $Al_2O_3$, $Na_2O$, MgO, $P_2O_2$ and $TiO_2$. Which components are selected depends upon the intended end-use of the coated medical or dental product.

Preparation of the surface of metal (e.g., titanium 100) can be done via various alternative means including: grit blasting; pickling; chemical milling/etching; ion ablation; reverse arc; water/liquid jet (with or without media); laser; or sonic.

The purpose of the surface ablation is to remove passivated and other metal compounds from the surface in preparation for coating. It is required for the metal surface (e.g., see FIG. 3) to have freely available bonds that will chemically join with the coating upon processing. These bonds are direct ionocovalent bonds (i.e., bonds having some degree of sharing and some degree of separation of electrons). Ionocovalent bonds are preferred as they are much stronger than Van Der Waals bonds, which can be easily removed in the shear direction. Enough surface of the substrate must be removed to ensure total removal of the passivated surface.

Applicants' preferred step of post-surface ablation cleaning is performed, preferably via ultrasonic baths, typically using an alcohol-based bath to remove foreign surface objects (e.g., residual dust, other particles and liquids) that may be present on the surface of the ablated metal. These foreign particles and liquids may be a by-product of the ablation cleaning. It is important to remove these foreign particles as they could foul the coating in several different ways depending upon the chemical constitution of the particle, the coating material and the surface. Fouling of the coating includes, but is not limited to, the following: burn up during coating firing producing a defect, reacting with the glass, or the surface, to create a defect, remain inertly on the surface to create a defect. Any residue may also promote coating delamination.

Applicants' preferred carrier or suspending fluid, as mentioned above, is made of 90%-99% propanol in organic alcohol. The ceramic (e.g., glass) preparation is then blended with the suspending fluid. A range of weight/volume percent is employed to facilitate layer application to achieve desired density and thickness. The solvent has a two-fold function: to carry the powder in suspension to the device; and to adhere the suspension to the device during and after it has been deposited (e.g., air-sprayed) onto the metal.

In the preferred embodiment, the coating step utilizes air spraying 110 at low pressure, typically 10 psi, to apply a uniform coating to the cleaned, ablated substrate surface 106. Other coating processes can be performed to achieve a uniform coating as well, such as: aerosol; dipping; and brushing.

The coated metal is then thoroughly dried in a relatively dust-free environment to assure the integrity of the final coating. This is to prevent subsequent process degradation. Drying times will vary based on thickness and composition of a sprayed coating. It is important to completely remove the alcohol to minimize the risk of volatilizing the alcohol during heating causing dynamic delamination of the coating.

Thermal processing is performed in a standard atmospheric furnace (i.e., a furnace with a controlled atmosphere and electric coils for radiant heat for firing) (not shown). This "atmosphere" is designed to prevent non-preferential bonding of the glass/ceramic to the metal substrate. Oxygen, nitrogen, or water can create compound(s) on the surface of the metal. That compound may prevent the melted glass from adhering and forming chemical bonds with the metal. The thermal cycle is determined by the type of glass used and its thermal characteristics.

It is important to design the firing and annealing processes for the coating to minimize thermally induced stresses. Using a biocompatible glass as a sample coating, the sequence for firing the implant or onplant is: insert a fully coated and dried component into an atmospheric furnace; purge the furnace of substantially all air, oxygen, nitrogen with an inert gas (preferably argon); fire the components to a glass transition temperature of the selected biocompatible glass; and slow cool the coated components to minimize stress between the glass and metal substrate.

Firing the coated substrate chemically forms the bond with the glass and metal. The glass may partly or fully vitrify, as appropriate for the product requirements, forming an engineered glass/ceramic. Using the improper atmosphere may create compounds that could be deleterious to the coating system. Alternatively, the preparation of the substrate can be performed by another effective method whose objective is to remove contaminants such as oxides, nitrides and carbides, on the surface of the metallic substrate to produce free bonds that will readily adhere to the biocompatible glass on firing in the inert atmosphere. Such methods include: pickling; chemical milling/etching; laser ablation; ion ablation; reverse arc; water/liquid jet (with or without media); and sonic.

The purging and firing of components using an inert gas is to preclude inadvertent creation/bonding of the undesirable compounds (e.g., metal oxides, nitrides) with the substrate prior to exposure to elevated temperatures and during elevated temperature exposure. Such inert gases include helium, neon, argon and other noble gases. Their outer shell of valence electrons is considered to be "full", giving them little tendency to participate in chemical reactions. It is important to prevent any new passive surface from forming as it will create a weak interface between the substrate and the coating. In this preferred embodiment, it is important to eliminate the possible titanium compounds that could minimize the chemical bond formed between the glass and the titanium.

Following thermal processing components were thoroughly evaluated to determine the strength of the bonding of glass to ceramic. Scratch testing was performed to characterize the strength of the bond. A micro-indenter was loaded, onto the surface, which was then pulled across the micro-indenter in the test used. All samples required significant force to remove glass/ceramic from titanium substrate. Samples showed no spallation with minor loading.

Samples were evaluated using a scanning election microscope. This testing was done by training the electrons in a scanning electron microscope in a line perpendicular to the coating and evaluating the x-rays that were emitted from that electron beam/material interaction. This test revealed intimate contact of glass to titanium metal. There was a gradual change of chemistry between the 290 micron and 305 micron regions in the line scan suggesting that a diffuse chemical interface that is on the order of 10-15 microns in thickness. It should be noted that compounds of oxygen or nitrogen were not detected at the interface.

Applicants' preferred process has many benefits, including: achieving a direct chemical bond between a biocompatible glass and a metal substrate (here, titanium); and producing a chemically pristine substrate with high free energy, free bonds. This process allows multiple layers of the biocompatible glass coating using spray techniques.

Figure 5:
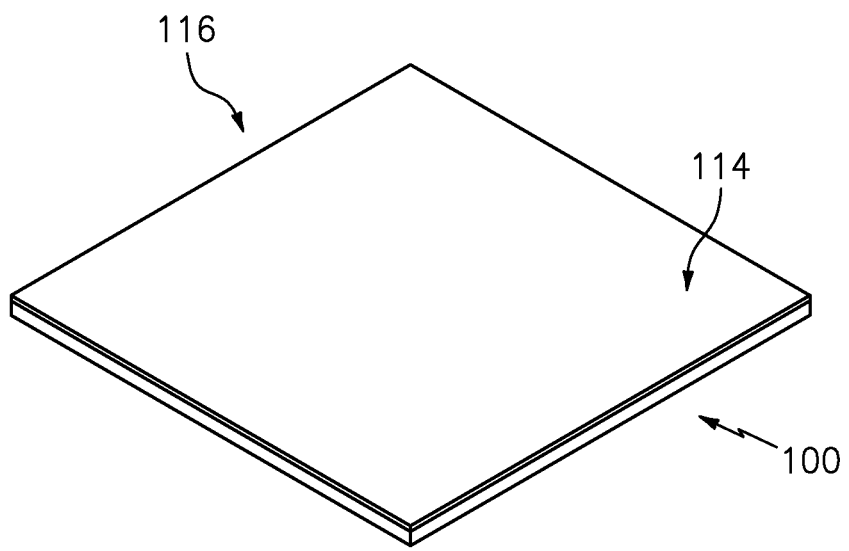
FIG. 5 depicts the coated substrate after being heat treated (fired) in an atmospheric furnace and subsequently cooled.

Note that FIG. 5 shows a flat piece of coated metal; that is only exemplary of Applicants' process. Since Applicants' process can be used with an implanted or onplanted implanted devices, the actual shape of the metal would be that of the covering for the device or component to be onplanted or implanted.

It should be understood by those skilled in the art that obvious modifications can be made without departing from the spirit of the invention. For example, a similar metal to titanium could be used. Reference therefore should be made primarily to the accompanying claims rather than the foregoing specification to determine the scope of the invention.

We claim:

1. A method of fusing a biocompatible and bioactive glass to a metallic substrate, the method comprising:
   a. grit blasting the metallic substrate to remove a surface layer of the metallic substrate to minimize the introduction of active foreign particles;
   b. cleaning the abrasion residue off the metallic substrate, after the grit blasting;
   c. creating a suspension of biocompatible and bioactive glass powders in a solvent;
   d. coating the metallic substrate with the suspension, after the cleaning, until the substrate is fully coated;
   e. drying thoroughly the suspension coated metallic substrate in a substantially dust-free environment to assure the integrity of the final coating;
   f. inserting the dried coated metallic substrate into a non-reactive chamber of an atmospheric furnace;
   g. purging the chamber with an inert gas to substantially remove any other gas within the chamber;
   h. firing the dried coated metallic substrate, inside the chamber, in the inert gas, to form a covalent bond between the metallic substrate and dried metallic substrate coating; and
   i. wherein steps d. through h. are sequential.

2. The method of claim 1 wherein the solvent is 90%-99% propanol in organic alcohol.

3. The method of claim 1 wherein the metallic substrate is titanium and, during the firing step h. of claim 1, a diffuse chemical interface between the titanium substrate and glass is formed with a thickness of 10 microns and 15 microns.

4. The method of claim 1 wherein a ceramic oxide is used as an abrasive for the grit blasting step.

5. A method process of fusing a biocompatible and bioactive glass to a metallic substrate, the method comprising:
   a. grit blasting a metallic substrate, comprised of titanium, with aluminum oxide to remove a passivated surface layer of the titanium substrate to minimize the introduction of active foreign particles;
   b. cleaning the metallic substrate thoroughly, after the grit blasting;
   c. creating a suspension of biocompatible and bioactive glass powders in a solvent;
   d. after the cleaning, depositing the suspension onto the metallic substrate with an air brush, until the substrate is fully coated;
   e. drying thoroughly the coated metallic substrate in air in a substantially dust-free environment to assure the integrity of the final coating;
   f. inserting the dried coated substrate into a non-reactive chamber of a furnace with a controlled atmosphere;
   g. purging the chamber with an inert gas to substantially remove any other gas within the chamber;
   h. firing the dried coated metallic substrate, inside the chamber, in the inert gas, to form a covalent bond between the metallic substrate and dried metallic substrate coating; and
   i. wherein steps d. through h. are sequential.

6. The method of claim 5 wherein the solvent is 90%-99% propanol in organic alcohol.

7. The method of claim 5 wherein the inert gas is argon.

8. The method of claim 5 wherein the coated metallic substrate is heated to at least a glass transition temperature of the biocompatible and bioactive glass.

9. The method of claim 5, during step h., a diffuse chemical interface between the titanium substrate and glass is formed with a thickness between 10 microns and 15 microns.

* * * * *